United States Patent [19]

Boudreau

[11] 4,199,238
[45] Apr. 22, 1980

[54] MINIATURE CAMERA PROBE

[76] Inventor: Jon P. Boudreau, 140 Hesperus Ave., Gloucester, Mass. 01930

[21] Appl. No.: 19,474

[22] Filed: Mar. 12, 1979

[51] Int. Cl.² .......................... A61B 1/04; G03B 29/00
[52] U.S. Cl. ........................................... 354/62; 128/6
[58] Field of Search .................. 354/62, 63; 128/4, 6, 128/8

[56] References Cited

U.S. PATENT DOCUMENTS

| 2,601,406 | 6/1952 | Marcouiller | 354/62 |
| 3,866,602 | 2/1975 | Furihata | 354/62 X |
| 4,038,977 | 8/1977 | Okada | 354/62 X |

Primary Examiner—John Gonzales
Attorney, Agent, or Firm—Joseph S. Iandiorio

[57] ABSTRACT

A miniature camera probe including an elongate housing; a fiber optic faceplate proximate a first end of the elongate housing; an aperture in the housing at one face of the fiber optic faceplate; a film holder in the housing at the other face of the fiber optic faceplate; a shutter in the elongate housing for controlling illumination of the faceplate through the aperture; a fiber optic light source extending in the elongate housing from the face of the fiber optic faceplate proximate the aperture to the other end of the elongate housing; and a shutter actuating device extending from the shutter to the other end of the elongate housing.

12 Claims, 5 Drawing Figures

MINIATURE CAMERA PROBE

FIELD OF INVENTION

This invention relates to a miniature camera probe, and more particularly to such a camera probe utilizing a fiber optic faceplate and light supply.

BACKGROUND OF INVENTION

There are a number of camera probe devices for obtaining images of objects which are difficult to reach and typically are quite small, such as in human bodies or in complex equipment. One such device consists simply of non-coherent fibers for delivering light from the accessible end of an elongate probe to the insertible end proximate the object to be examined, and coherent fibers for returning the image back to a film or viewer at the accessible end. Typically in such devices the fiber optic pads are a minimum of one hundred twenty-five mils in diamater and are very expensive. In another device, similar bundles of fiber optic rods are used to provide light and transmit the image with the addition of a right angle prism at the remote end of the probe. The probe is inserted all the way into a passage, then withdrawn at a predetermined uniform speed, causing the prism to scan the surface of the passage . An imaging system at the accessible end of the probe projects the moving image onto film being moved at a synchronized speed to record the image. The image on the film shows the lines resulting from the scanning action and the resolution is not high, usually about ten mils. In yet another device, fiber optics are used for illumination and a glass rod with lenses on each end is used for imaging. These devices are generally limited to less than a foot in length, are not flexible, and are quite expensive.

SUMMARY OF INVENTION

It is therefore an object of this invention to provide a simple, inexpensive, and improved miniature camera probe.

It is a further object of this invention to provide such a camera probe which provides high resolution.

It is a further object of this invention to provide such a camera probe which may be extremely long, quite narrow, thin, and flexible.

This invention features a miniature camera probe having an elongate housing and a fiber optic faceplate proximate a first end of the elongate housing. There is an aperture in the housing at one face of the fiber optic faceplate and a film holder in the housing at the other face of the fiber optic faceplate. A shutter in the elongate housing controls the exposure of the film through the faceplate and aperture. The fiber optic light source extends in the elongate housing from the face of the fiber optic faceplate near the aperture to the other end of the elongate housing. A shutter actuating device extends from the shutter to the other end of the elongate housing.

In one embodiment, the faceplate is formed of a plurality of fiber optic elements, and the numerical aperture of those elements is 0.4 or less. The diameter of the elements may be approximately two-tenths mil, and the distance between the faceplate and the outside of the housing measured through the aperture may be approximately four mils. The fiber optic elements may be inclined to the film plane to produce an angled photograph which together with a second complementary angled photograph is useful for constructing a stereoscopic image. The fiber optic light source may include a plurality of 5-mil fiber optic rods, and the housing may be elongate in a first dimension, narrow in a second dimension, and thin in a third dimension, the dimensions being all mutually perpendicular.

A recess in the housing is provided to receive the film holder and faceplate. The shutter may include a shutter member slidable away from the end of the fiber optic light source which is near the faceplate to uncover the aperture. The edge of the shutter member which faces the end of the fiber optic light source may be inclined to aid reflection, through the aperture toward the object to be photographed, of the light coming from the fiber optic light source. A transparent member may be mounted following the shutter member to cover the faceplate during exposure. The shutter actuator may include one or more rod members attached to the shutter and disposed along the elongate housing, from the shutter to the other end of the housing.

DISCLOSURE OF PREFERRED EMBODIMENT

Other objects, features and advantages will occur from the following description of a preferred embodiment and the accompanying drawings, in which.

The invention may be accomplished with a miniature camera probe that includes an elongate housing which is also generally narrow and thin. There is a fiber optic faceplate near a first end of the elongate housing with an aperture in the housing communicating with one face of the fiber optic faceplate. A film holder in the housing communicates with the other face of the fiber optic faceplate.

A shutter controls the exposure of the film through the faceplate. A fiber optic light source extends in the housing from the face of the fiber optic faceplate to the other end of the elongate housing and supplies light from that other end to the area of the faceplate and aperture, for illuminating the object to be photographed when the shutter is open. A shutter actuating device extends from the shutter to the other end of the elongate housing to enable the user to actuate the shutter and operate the camera at a remote distance from the tip of the probe when it is inserted in a passage to be photographed.

Figure 1:
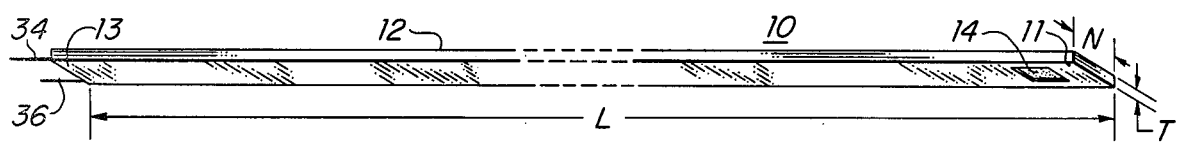
FIG. 1 is an axonometric view of a miniature camera probe according to this invention.
Figure 2:
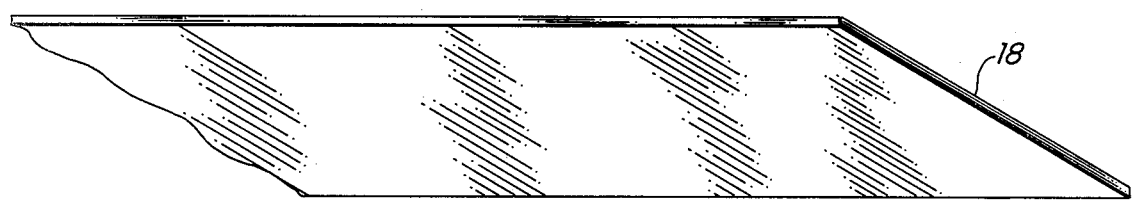
FIG. 2 is an exploded axonometric view of the end of the camera probe of FIG. 1 showing the camera mechanism.
Figure 2:
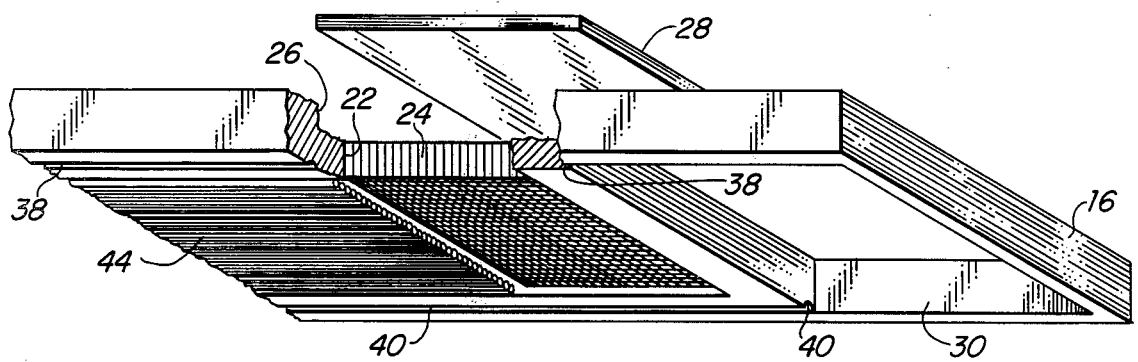
Figure 2:
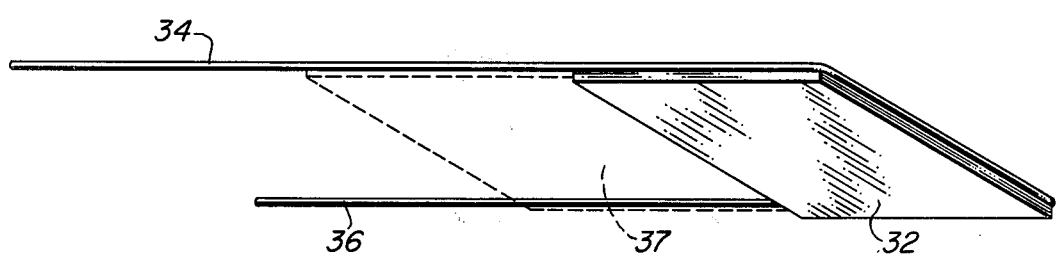
Figure 2:
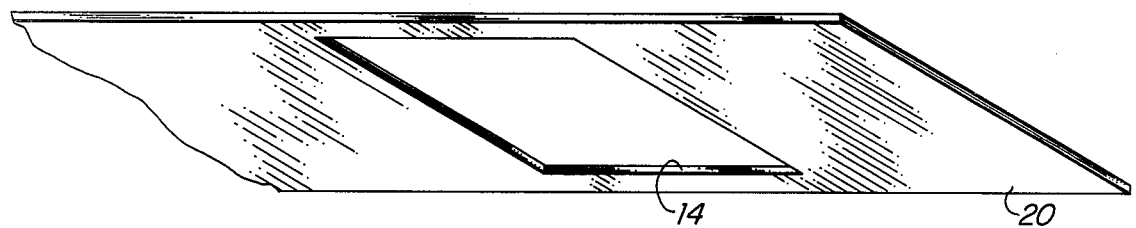

There is shown in FIG. 1 a miniature camera probe 10 and an elongate housing 12 having an accessible end 13 and insertible end 11 provided with an aperture 14 for exposing film in the camera inside housing 12. Wire rods 34, 36 actuate a shutter at aperture 14. Housing 12 is generally quite long in the "L" dimension, narrow in the "N" dimension, and thin in the "T" dimension. Housing 12 includes a body 16, FIG. 2, top cover 18, and bottom cover 20, which includes aperture 14. Aligned with aperture 14 in body 16 is a recess 22 which contains fiber optic faceplate 24. Recess 22 is enlarged at its upper end to form film holder 26 for receiving film 28. a second recess 30 in body 16 receives shutter 32 when it is moved away from aperture 14 to uncover faceplate 24 and expose film 28. Shutter or plate 32 is moved by means of a shutter actuator mechanism, a pair of wires 34, 36, which are fixed to it and are received in channels 38 and 40, respectively, in body 16. Illumination of the object to be photographed through aperture 14 when shutter 32 is in the open position is supplied by fiber optic rods 44 which bring light from the accessible end 13 to the insertible end 11. The space adjacent shutter or plate 32 need not be empty as shown; it may contain a transparent plate 37 through which exposure occurs.

Figure 3:
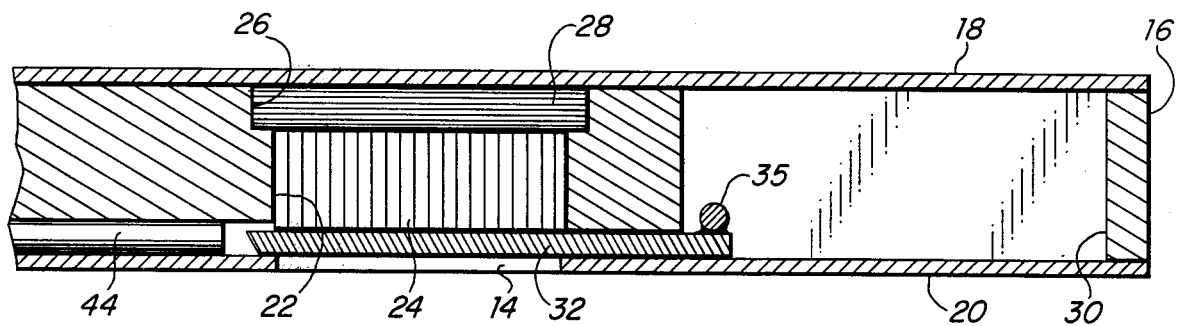
FIG. 3 is a side elevational cross-sectional view of generally the same portion of the camera probe shown in FIG. 2.
Figure 4:
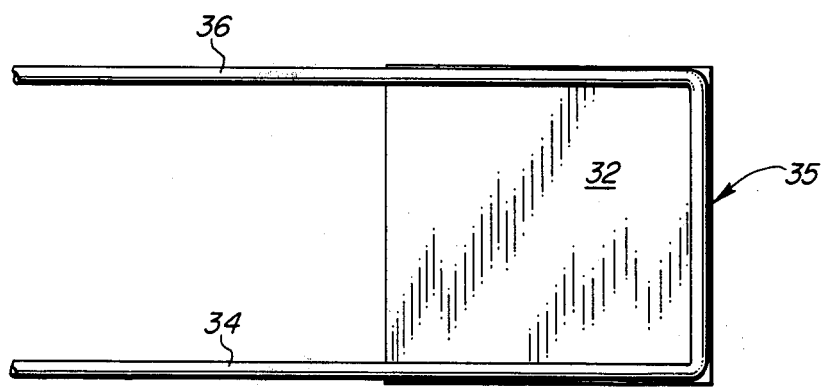
FIG. 4 is a top plan view of a portion of the shutter and shutter actuating device shown in FIGS. 2 and 3.

In a preferred embodiment, camera probe 10 is approximately five feet long, three-quarters of an inch wide in the N dimension, and about thirty-thousandths of an inch thick in the T dimension. Top cover 18, FIG. 3, is made of cold rolled steel three-quarters of an inch wide and one thousandth of an inch thick. Bottom cover 20 is made of the same material with a one-half inch square cutout centered in it to form aperture 14. Body 16 is cold rolled steel three-quarters of an inch wide and thirty thousandths of an inch thick. Recess 22 and fiber optic faceplate 24 are approximately one-half inch square and twenty thousandths of an inch thick, while the film holder portion 26 of recess 22 is approximately eight thousandths of an inch thick and one-half inch wide in the N dimension and about three quarters of an inch long in the L dimension. A typical Polaroid film to be placed in the holder is approximately seven thousandths of an inch thick. Fiber optic light supply 44 is composed of a number of five-mil optical fibers made of glass or plastic. Recess 30 is approximately three-quarters of an inch in the L direction and six tenths of an inch in the N dimension, and may be twenty thousandths of an inch deep or deeper. Shutter 32 may be four thousandths of an inch thick and approximately three quarters of an inch in the L dimension and six tenths of an inch in the N dimension. Wires or rods 34 and 36 may be formed of a single twenty mil stainless steel wire 35 bent in a U shape and fastened to shutter 32.

Figure 5:
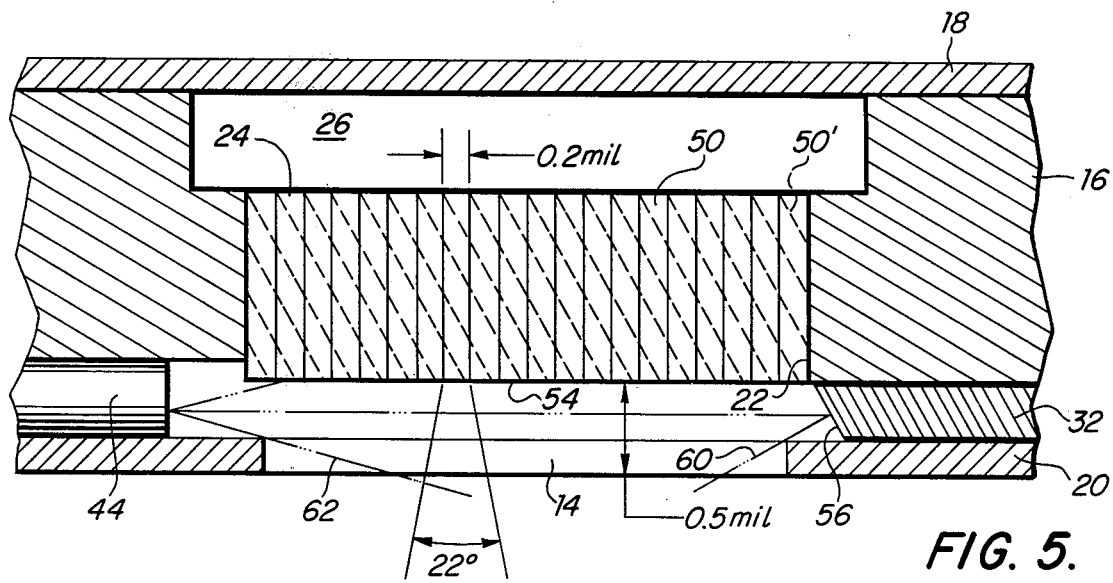
FIG. 5 is an enlarged detail view showing certain optical features of the camera probe.

Fiber optic faceplate 24, FIG. 5, may include a plurality of fiber optic elements 50 made of plastic or glass optical fiber so that their numerical aperture, that is the ratio of the index of refraction of the rod 50 to the index of refraction of the coating 52, is 0.4 or less, and preferably 0.3 or less. For example, with the glass used for fiber optic element 50 in which the core has the index of refraction $n_1$ equal to 1.5 and the clad has the index of refraction $n_2$ equal to 1.484, the numerical aperture is 0.35.

With these specific materials and the rods sized at five mils long and 0.2 mils in diameter, there is produced a cone angle, or angle of reception, of approximately 22°. These characteristics of the fiber optic faceplate 24 coupled with a distance of four or five mils from the face 54 of faceplate 24 proximate aperture 14 to the aperture 14 results in a resolution of approximately one thousandth of an inch, and perhaps greater, even to five ten-thousandths of an inch.

Also, as shown in FIG. 5, the edge 56 of shutter 32 may be inclined so that light rays 60 as well as light rays 62 will be reflected down through aperture 14 to illuminate the object to be photographed. In addition, rods 50 may be inclined as at 50′ to produce an angled photograph of an area which together with a second complementary angled photograph of the area is useful to produce stereoscopic images.

Although specific dimensions have been given in terms of length, width, and thickness for the camera probe according to this invention, these are not a necessary limitation of the invention, as the probe may be made longer or shorter, and of course may be made thinner and more narrow, if a smaller, more nearly square or round cross section is desirable.

Other embodiments will occur to those skilled in the art and are within the following claims:

What is claimed is:

1. A miniature camera probe comprising:
   an elongate housing;
   a fiber optic faceplate proximate a first end of said elongate housing;
   an aperture in said housing at one face of said fiber optic faceplate;
   a film holder in said housing at the other face of said fiber optic faceplate;
   a shutter in said elongate housing for controlling illumination of said faceplate through said aperture;
   a fiber optic light source extending in said elongate housing from the face of said fiber optic faceplate proximate said aperture to the other end of said elongate housing; and
   a shutter actuating device extending from said shutter to said other end of said elongate housing.

2. The miniature camera probe of claim 1 in which said faceplate is formed of a plurality of fiber optic elements.

3. The miniature camera probe of claim 2 in which the numerical aperture of said elements is 0.4 or less.

4. The miniature camera probe of claim 2 in which the diameter of said elements is approximately two tenths of a mil and the distance between the faceplate and outside of the housing is approximately four mils.

5. The miniature camera probe of claim 1 in which said fiber optic light source includes a plurality of five mil fiber optic rods.

6. The miniature camera probe of claim 1 in which said housing is elongate in a first dimension, narrow in a second dimension, and thin in a third dimension which are all mutually perpendicular.

7. The miniature camera probe of claim 1 in which said housing includes a recess in which said film holder and faceplate are disposed.

8. The miniature camera probe of claim 1 in which said shutter includes a shutter member which is slidable away from the end of said fiber optic light source proximate said faceplate to uncover said aperture.

9. The miniature camera probe of claim 8 in which the edge of said shutter member facing the end of said fiber optic light source proximate said faceplate is inclined to aid reflection of the light from the fiber optic light source through the aperture toward the object to be photographed.

10. The miniature camera probe of claim 1 in which said shutter actuator includes one or more rod members attached to said shutter and disposed along said elongate housing from said shutter to the other end of said housing.

11. The miniature camera probe of claim 1 in which there is a transparent member adjacent said shutter member through which exposure occurs when said shutter member is opened.

12. The miniature camera probe of claim 2 in which said fiber optic elements are inclined to the plane of the film and shutter.

* * * * *